United States Patent [19]
Doss

[11] Patent Number: 5,015,952
[45] Date of Patent: May 14, 1991

[54] APPARATUS FOR CHARACTERIZING CONDUCTIVITY OF MATERIALS BY MEASURING THE EFFECT OF INDUCED SHIELDING CURRENTS THEREIN

[75] Inventor: James D. Doss, Los Alamos, N. Mex.
[73] Assignee: University of California, Alameda, Calif.
[21] Appl. No.: 324,264
[22] Filed: Mar. 14, 1989

Related U.S. Application Data

[63] Continuation-in-part of Ser. No. 181,451, Apr. 13, 1988.
[51] Int. Cl.$^5$ ............ G01N 27/72; G01R 33/12; G01R 33/035; G01C 21/08
[52] U.S. Cl. ............................ 324/236; 324/654; 505/843
[58] Field of Search ............ 324/236, 248, 719, 654, 324/655, 658, 667, 668, 681, 682; 505/842, 843

[56] References Cited

U.S. PATENT DOCUMENTS 3,036,267  5/1962  Semelman ............... 324/236
3,477,018  11/1969  Richardson et al. ........... 324/236
4,000,458  12/1976  Miller et al. ................. 324/719

OTHER PUBLICATIONS

Lyneis et al., "Measurement of the Microwave Properties of Superconducting $N_{630}$–$Ta_{70}$", IEEE Transactions on Magnetics, vol. Mag-13, No. 1, Jan. 1977, pp. 339–342.

Primary Examiner—Walter E. Snow
Attorney, Agent, or Firm—Samuel M. Freund

[57] ABSTRACT

Apparatus and method for noncontact, radio-frequency shielding current characterization of materials. Self- or mutual inductance changes in one or more inductive elements, respectively, occur when materials capable of supporting shielding currents are placed in proximity thereto, or undergo change in resistivity while in place. Such changes can be observed by incorporating the inductor(s) in a resonant circuit and determining the frequency of oscillation or by measuring the voltage induced on a coupled inductive element. The present invention is useful for determining the critical temperature and superconducting transition width for superconducting samples.

6 Claims, 10 Drawing Sheets

APPARATUS FOR CHARACTERIZING CONDUCTIVITY OF MATERIALS BY MEASURING THE EFFECT OF INDUCED SHIELDING CURRENTS THEREIN

The United States Government has rights in this invention pursuant to Contract No. W-7405-ENG-36 between the U.S. Department of Energy and the University of California.

BACKGROUND OF THE INVENTION

This patent application is a continuation-in-part of pending U.S. patent application Ser. No. 07/181,451, filed Apr. 13, 1988.

The present invention relates generally to eddy current measurements and, more particularly, to noncontact apparatus and method for characterization of conductivity of materials using changes in induced voltages or changes in frequency of oscillation of coupled inductive elements surrounding the material to be characterized.

Interest in high temperature superconducting materials has grown dramatically. With this interest has developed a need for simple, noncontact conductivity characterization techniques, since the attachment of electrical contacts to samples (especially thin films) is difficult and often significantly modifies the material in the region of the junction. "Screening" or "shielding" currents form when a superconducting material is subjected to external magnetic fields. These currents are similar to eddy currents in conducting materials except that eddy currents die away, while "screening" currents do not.

Mutual and self-inductance techniques have been used for many years for measuring resistivity and susceptibility. For example, J. D. Crowley and T. A. Rabson in "Contactless Method of Measuring Resistivity," Rev. Sci, Instrum. 47, 712 (1976), report a system which uses induced currents for measuring resistivity without making electrical contact to a sample. A primary coil is separated axially from a secondary coil and the sample is inserted between them. The voltage induced in the secondary coil is due not only to the driving magnetic field of the primary coil, but also to the magnetic field of the currents induced in the sample. These two magnetic fields are 90° out of phase. A lock-in amplifier with a phase-sensitive mixer suppresses the driving field induced voltage and measures the quadrature signal due to the induced currents. The frequency dependence of the induced voltage has been measured between 1 and 40 kHz. The authors state that the primary factors limiting the extension of their technique to high resistivity ranges are the frequency limitations of the phase-sensitive detector and the relative magnitude of the capacitive coupling effect compared to the induced current effect. Since the induced voltage varies as the square of the frequency of the applied current, it would be advantageous to make measurements at higher frequencies. Additionally, the authors teach the use of four coils as coupled-inductor bridges. A paper by R. B. Goldfarb and J. V. Minervini, entitled "Calibration Of AC Susceptometer For Cylindrical Specimens," Rev. Sci. Instrum. 55, 761 (1984), discloses the measurement of the absolute magnitude of the magnetic susceptibility of cylindrical specimens using an ac susceptometer whose calibration is based on a calculation of mutual inductance. The apparatus and measurement is similar to that of Crowley and Rabson.

In A. L. Schawlow and G. E. Devlin, "Effect of the Energy Gap on the Penetration Depth of Superconductors," Phys. Rev. 113, 120 (1959), the authors report the measurement of the dependence on temperature of the low-frequency (100 kHz) method where the sample under investigation serves as the core of a solenoid whose inductance changes with the penetration depth. The coil is resonated by a capacitor and the combination forms the tank circuit of an oscillator. The inductance therefore controls the frequency of an oscillator which can be measured precisely, since a change in the penetration depth shifts the frequency of the oscillator. Basically, the method of Schawlow and Devlin is a self-inductance measurement. The authors teach further that the solenoid must be immersed in the cooling liquid since the sample to be investigated must closely match the volume of the solenoid.

An apparatus operating at 2-3 MHz, capable of measuring upper critical fields of thin (micron size) superconducting platelets has been discussed by B. J. Dalrymple and D. E. Prober in "Upper Critical Fields of the Superconducting Layered Compounds $Nb_{1-x}Ta_x$-$Se_2$," Journal of Low Temperature Physics 56 Nos. 5/6, 545-574 (1984).

There is no teaching in the art concerning the measurement of the critical temperature of materials on arbitrary substrates (especially large flat surfaces such as thin films) at high frequencies. Even superconducting resonant cavity methods, which provide similar data using a different technique, cannot be used where ordinary substrates are exposed to the cavity field. This is especially important since many of the application for the high temperature superconducting materials (that is, computers, general electronics, accelerator cavities, etc.) will require operation at frequencies in excess of 1 GHz. Therefore, such superconducting materials will have to be characterized at these frequencies.

Accordingly, it is an object of the present invention to characterize the conductivity of materials without making electrical contact therewith, including cases where the conductor is attached to a lossy substrate.

Another object of the present invention is to characterize the conductivity of materials at high frequencies without making electrical contact therewith.

Yet another object of my invention is to characterize the region of the critical temperature of superconducting materials without making electrical contact therewith.

Still another object of my invention is to characterize the region of the critical temperature of superconducting materials at high frequencies without making electrical contact therewith.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus of this invention includes an electronic oscillator having a series-resonant LC circuit, the inductive member thereof including a first inductive element, and a second inductive element in series-connection with the first inductive element and disposed generally in opposition to the first inductive element, the material under investigation being located between the two inductive elements, and a frequency counter for measuring the frequency of oscillation of the electronic oscillator.

Preferably, the electronic oscillator includes at least one capacitive element in series connection with the inductive member, and at least one electronic amplifier in series connection with the inductive member and the at least one capacitive element.

It is preferred that the first inductive element and the second inductive element include substantially flat wire coils having the axis thereof substantially colinear.

Preferably also, the area of the substantially flat wire coils are not large compared with the physical dimensions of the material under investigation.

It is also preferred that the present apparatus includes cooling means for bringing the material under investigation to a chosen temperature, temperature measuring means for determining the temperature of the material under investigation, and a vacuum chamber for enclosing the first inductor, the second inductor, the cooling means, the temperature measuring means, and the sample under investigation and for providing a reduced pressure environment therefor.

In a further aspect of the present invention, in accordance with its objects and purposes, the apparatus hereof includes a first inductive element, a second inductive element disposed generally in opposition to the first inductive element, the superconducting material under investigation being located between the inductive elements, oscillatory signal generating means for driving the first inductive element, voltage monitoring means for measuring the voltage impressed on the second inductive element, cooling means for bringing the superconducting material under investigation to a chosen temperature, temperature measuring means for determining the temperature of the superconducting material under investigation, and a vacuum chamber for enclosing and for providing a reduced pressure environment for the first inductive element, the second inductive element, the cooling means, the temperature measuring means, and the superconducting material under investigation.

In yet a further aspect of the present invention, in accordance with the objects and purposes, the method hereof includes the steps of placing the material under investigation between two coupled inductive elements, cooling the material, exciting one of the two inductive elements with an ac signal, and measuring the voltage induced on the second inductive element.

Preferably, each inductive element is adjusted to resonate at the frequency of the ac signal employed in the step of exciting one of the two inductive elements.

In still a further aspect of the present invention, in accordance with the objects and purposes, the method hereof includes the steps of placing the material under investigation between two, series-connected, coupled inductive elements, cooling the material, causing the inductive elements to undergo sustained electronic oscillation, and measuring the frequency of electronic oscillation.

In another aspect of my invention, in accordance with the objects and purposes, the apparatus hereof includes a wire loop antenna located in proximity with the material under investigation, a series capacitor in electrical connection with the wire loop antenna for forming a resonant circuit therewith, a series-connected amplifier which oscillates in combination with the series capacitor and loop antenna, a capacitive probe for remotely measuring the frequency of resonance of the oscillating resonant circuit, cooling means for bringing the superconducting material under investigation to a chosen temperature, temperature measuring means for determining the temperature of the superconducting material under investigation, and a vacuum chamber for enclosing and for providing a reduced pressure environment for the wire loop antenna, the capacitive probe, the cooling means, the temperature measuring means, and the superconducting material under investigation.

In yet another aspect of my invention, in accordance with the objects and purposes, the apparatus hereof includes a wire loop antenna located in proximity with the material under investigation, the wire loop having one end grounded, a series-connected amplifier which oscillates in conjunction with the wire loop, the amplifier input being driven by a parallel electrical connection on the wire loop antenna, a capacitive probe for remotely measuring the frequency of resonance of the resonant circuit, cooling means for bringing the superconducting material under investigation to a chosen temperature, temperature measuring means for determining the temperature of the superconducting material under investigation, and a vacuum chamber for enclosing and for providing a reduced pressure environment for the wire loop antenna, the capacitive probe, the cooling means, the temperature measuring means, and the superconducting material under investigation.

In still another aspect of the present invention, in accordance with its objects and purposes, the apparatus hereof includes a single-coil induction sensor located in proximity to the material under investigation, the induction sensor being the inductive element in a series-resonant LC circuit which is included in an electronic oscillator, and a frequency counter for measuring the frequency of the electronic oscillator. The oscillator sensors may be much smaller than the material.

Preferably, the electronic oscillator is comprised of a closed loop containing at least one capacitive element in series connection with the induction sensor, and at least one electronic amplifier in series connection with the induction sensor.

It is also preferred that the induction sensor be movable over the surface of the sample.

Benefits and advantages of the present invention include the absence of electrical contact with the material under investigation, low noise and high resolution, the measurement of bulk characteristics of the material, as opposed to filamentary conduction which is seen in dc resistivity measurements, rapid measurements (characterization in a resonant cavity that typically takes ~10 times longer), insensitivity to sample geometry, and high frequency measurement capability.

BRIEF DESCRIPTION OF THE DRAWINGS

The accompanying drawings, which are incorporated in and form a part of the specification, illustrate five embodiments of the present invention and, together with the description, serve to explain the principles of the invention. In the drawings:

FIG. 9a is a schematic representation of the single-coil oscillator frequency-shift embodiment of the present invention as applied to the characterization of superconducting samples, while

DETAILED DESCRIPTION OF THE PREFERRED EMBODIMENTS OF THE INVENTION

Briefly, the present invention permits the determination of the critical temperature and the width of the transition region for high-temperature superconducting materials in the frequency range between 5 MHz and 1 GHz. The invention can be generalized to include the characterization of resistivity of any sample. The technique involves locating the sample adjacent to one or more inductors that form part of a resonant LC circuit, measuring changes in self-inductance (or mutual inductance when more than one inductor is involved) as a function of sample temperature, as shielding current flow is affected by changes in conductivity. The sample and inductor(s) are placed in a vacuum chamber, the sample being cooled by a copper "cold finger" that is itself cooled with liquid helium. The inductor(s) remain at room temperature.

In one embodiment of my invention, a pair of coupled sensing coils are series-connected and used as the inductive member of a series-resonant LC circuit in an electronic oscillator. When the sample is located between the coils, the oscillation frequency varies as a function of sample resistivity. This method is capable of high resolution. Accuracy is limited by drift of the oscillator. Tests show long-term drift is less than 1 KHz/hour and short-term oscillator (frequency-modulation) noise is less than ±50 Hz for an uncompensated oscillator. These errors are relatively small when compared to typical sample-induced frequency shifts (i.e., 50 kHz to 1000 kHz, depending on sample size).

In an induced-voltage measurement embodiment of the present invention, a change of mutual inductance is detected between a pair of disc-shaped sensing coils, by changes in resistivity of a sample placed between the coils. That is, mutual inductance is modified by resistivity changes in the sample which alter the coupling and change the level of voltage induced by a primary on a secondary inductor. Therefore, the relative magnitude of voltage induced in the secondary coil, measured with a digital storage oscilloscope, is a function of sample conductivity; a steep slope is an indication of the superconducting transition.

A single sensing coil may be used. Experiments with a single-turn inductor adjacent to copper and aluminum foils indicate that this approach can be used at frequencies in excess of 1.5 GHz. This single-coil, self-inductance method is particularly well-suited to large area films, films plated on thick substrates, or films deposited on the inner walls of cavities.

Figure 1:
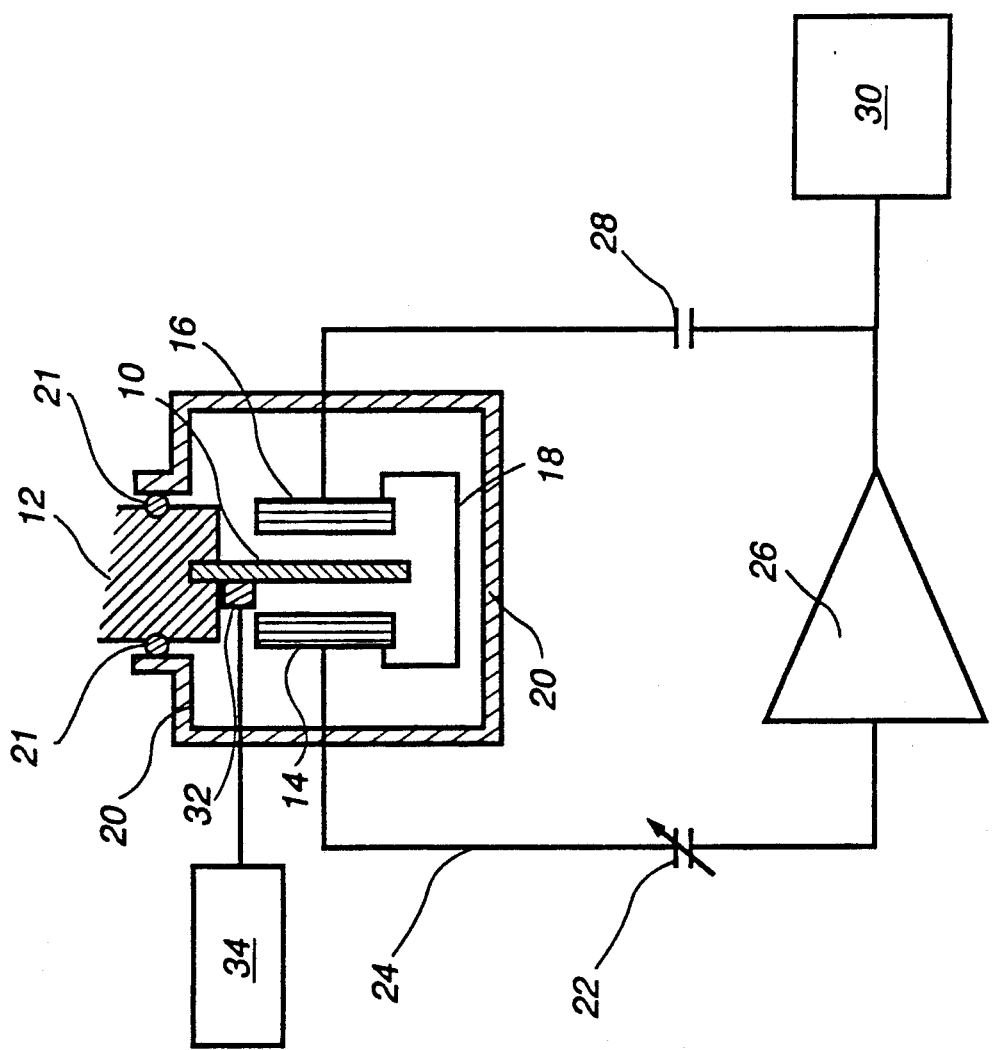
FIG. 1 is a schematic representation of the oscillator frequency-shift embodiment of the present apparatus as applied to the characterization of superconducting samples.

Reference will now be made in detail to the present preferred embodiments of the invention, examples of which are illustrated in the accompanying drawings. Identical call-outs are used throughout to identify similar or identical structure. Turning now to FIG. 1, a schematic representation of the oscillator frequency-shift embodiment of the present apparatus is shown. Superconducting sample 10 is cooled by cold finger 12 which is in turn cooled using liquid helium. The sample 10 is placed between two, generally flat inductor coils 14 and 16 which are series connected by wire 18. The sample, the cold finger, and the coils are located within vacuum enclosure 20, sealed with o-ring 21 which provides a reduced-pressure environment for these components.

The value of mutual inductance is indirectly measured as follows. The presence of shielding currents in sample 10 tends to reduce the magnitude of mutual inductance (M) between coils 14 and 16 where the total inductance is;

$$L_T = L_1 + L_2 \pm 2M$$

where $L_1$ and $L_2$ represent the self-inductance of coils 14 and 16, respectively. The + or − sign may be selected for the 2M term by winding the coils in either a flux-aided or flux-opposing mode, respectively. It was decided to employ the flux-aided mode so that as M is decreased (at lower temperatures due to increasing shielding current levels), $L_T$ also decreases. Coils 14, 16 (with effective inductance $L_T$) are connected in series with a resonating capacitance 22, the combination may be used as the frequency-determining LC circuit in the regenerative feedback path of an oscillator 24. Amplifier 26 and dc blocking capacitor 28 complete the oscillator 24 circuitry. Capacitor 28 is much larger than capacitor 22 so that only the value of capacitor 22 has a substantial effect on resonance. While the frequency of oscillation will be affected by the phase shift of the oscillator's active circuitry, stray capacitance, etc., the approximate frequency (f) of operation is:

$$f \approx \frac{1}{2\pi \sqrt{L_T C_R}}$$

$C_R$ is approximately equal to resonating capacitance 22. $L_T$, as indicated above, is a function of mutual inductance (M), which in turn is a function of the level of shielding currents induced in sample 10. The level of induced shielding current is a function of sample resistivity ($\rho$), so that the oscillator frequency is a function of sample resistivity:

$$f = f(\rho)$$

The oscillation frequency is then measured by electronic counter 30 while the temperature of the sample is changed through the range of interest which is typically 20 K to 300 K for high temperature superconducting samples.

Sample temperature was measured in each instance with carbon-glass resistor 32 calibrated by the manufacturer to 0.01 K and displayed on reader 34. Linear interpolation introduced errors that were less than ±1 K. To minimize any effects due to nonuniform sample temperature, frequency measurements were made with a temperature change of about 1 K/minute. The oscillator frequency is altered by sample resistivity.

Figure 2:
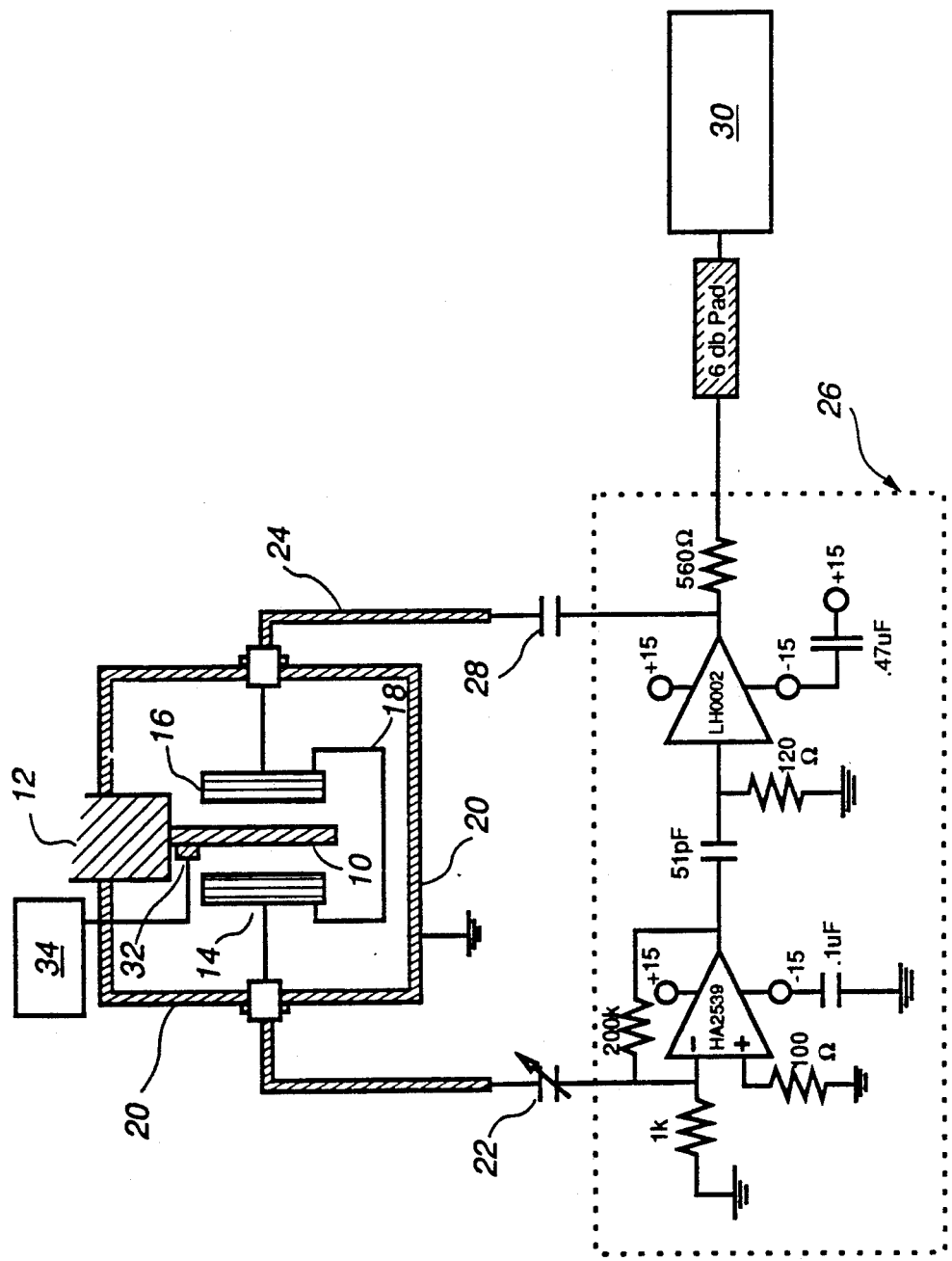
FIG. 2 is a more detailed schematic representation of the embodiment of the apparatus shown in FIG. 1 hereof, showing the details of the amplifier and measurement circuitry.

FIG. 2 is a more detailed schematic representation of the embodiment of my apparatus shown in FIG. 1 hereof and generally described hereinabove. Coils 14 and 16 are 20 turns of 32 gauge copper wire and have a 5–6 mm face diameter. The coil separation is approximately 5 mm. This two-coil arrangement provides minimum sensitivity to sample motion, especially when the sample is near the center point between the coils. Capacitance 22 is adjusted for resonance at about 16 MHz, and a typical measurement yields a frequency shift of 500 kHz at the superconducting transition temperature. In the situation where the sample is not self-supporting, it may be "sandwiched" between sheets of nonconducting material such as sapphire. In other cases, such as with thin films, the superconductor may be mounted on relatively lossy dielectrics.

Figure 3:
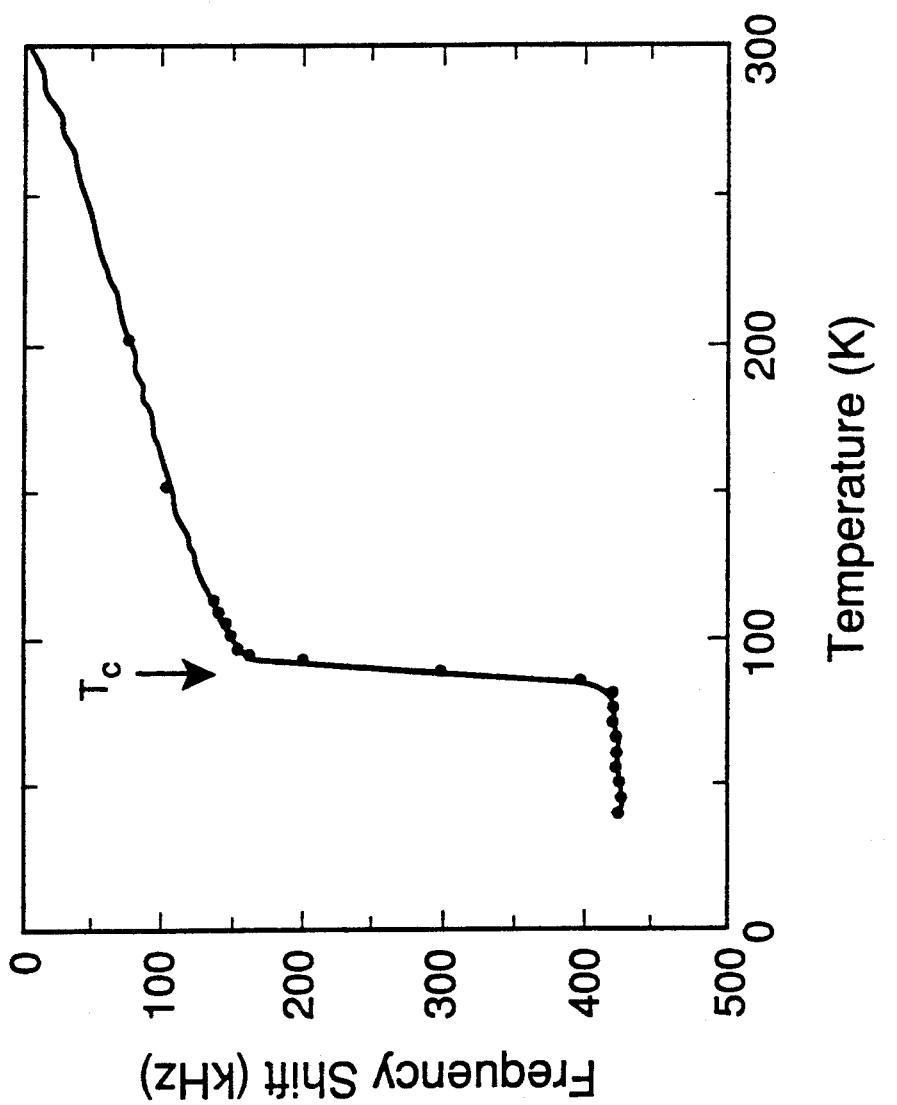
FIG. 3 shows a trace of the shift in the oscillator frequency as a function of superconducting material sample temperature.

FIG. 3 shows a trace of a measurement taken using the apparatus described in FIG. 2 hereof on a superconducting sample of $YBa_2Cu_3O_x$. Plotted is the frequency shift of oscillator 24 as a function of sample temperature. The critical transition temperature ($T_c$) is identified on the trace.

Figure 4:
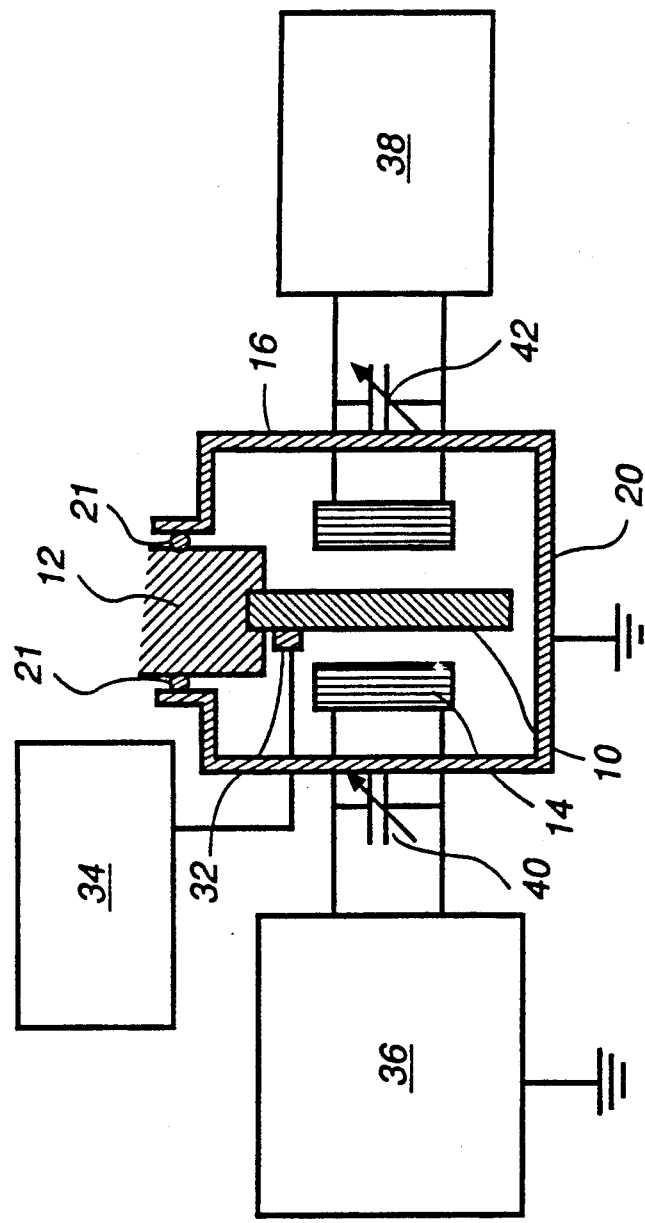
FIG. 4 is a schematic representation of the induced-voltage measurement embodiment of my invention.

FIG. 4 shows a schematic representation of the induced-voltage measurement embodiment of the present invention. Structures similar or identical to that of FIGS. 1 and 2 are denoted by the same call-out numbers. A plot of output voltage across coil 16 versus temperature for a sample is what one would expect for a plot of ac resistivity versus temperature.

In this approach, a high-temperature superconducting sample 10 is placed between two coupled inductive sensors 14, 16. An rf signal source 36 drives the primary sensor coil 14 and the second coil 16 is monitored with a device 38 for measuring the induced voltage. A digital storage oscilloscope, voltmeter, etc. may be utilized. Each coil is resonated at the chosen frequency of operation using tuning capacitors 40 and 42, respectively; this increases coupling and sensitivity. When sample resistivity is high (i.e., at room temperature, ~300 K for a superconducting sample), or when a ceramic sample (or a very thin niobium film) is measured, the output is generally higher than it will be at lower temperatures. As the sample resistance decreases (T reduced from 300 K to 20 K for a high-temperature superconducting sample), shielding currents induced in the high-temperature copper-oxide superconducting sample generate an electromagnetic field that tends to cancel the field induced in the secondary coil. Thus, as a sample approaches the critical temperature (~90 K), voltage on the secondary decreases due to increased levels of "shielding" in the sample. As the superconducting material passes through the transition to very low ac resistivity, the secondary coil is shielded from the primary by the material. The extent of the shielding is a function of the size of the sample in relation to coil size and spacing. Generally, to improve the accuracy and sensitivity of the measurements, the coil dimensions should not be large compared to the major sample dimensions for all embodiments of my invention.

Figure 5:
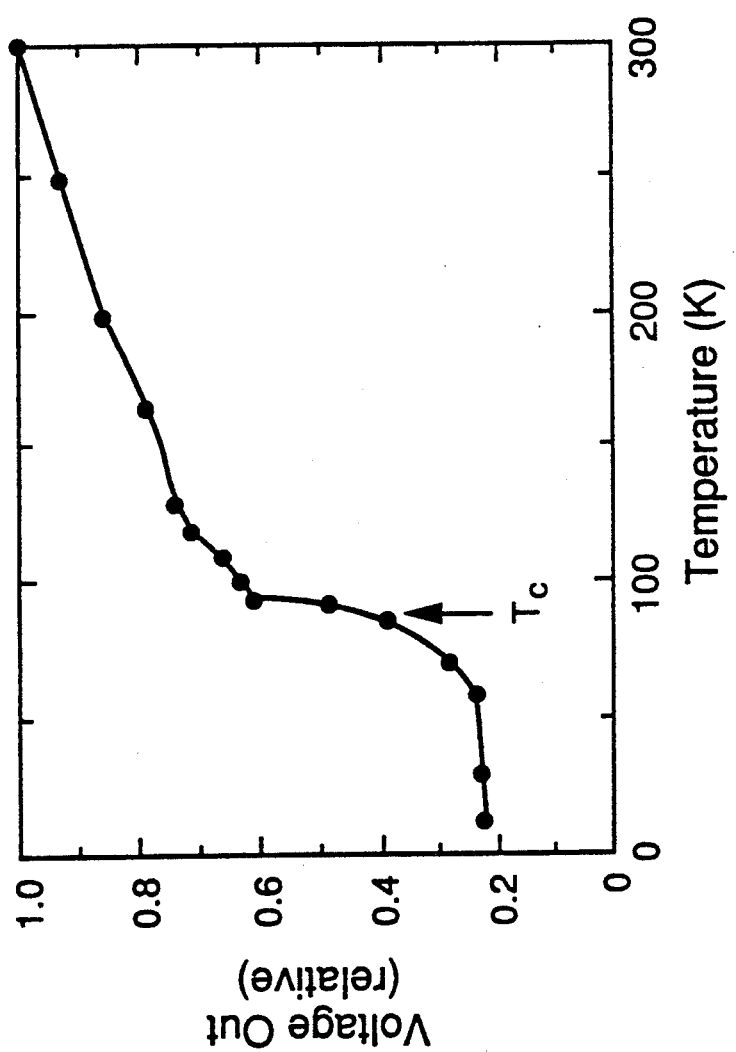
FIG. 5 shows a trace of the output voltage of the sensor inductor as a function of superconducting material sample temperature.

FIG. 5 shows a trace of the output voltage of sensor inductor 16 as measured on voltage measuring device 38 as a function of sample temperature for $GdBa_2Cu_3O_x$ superconducting material. Each coil employed was resonated at about 8 MHz and was fabricated from 10 turns of 26 gauge copper wire. The coil face diameter was 1 cm and the coils were spaced 1 cm apart. The value of critical transition temperature ($T_c$) is indicated in FIG. 5.

Figure 6:
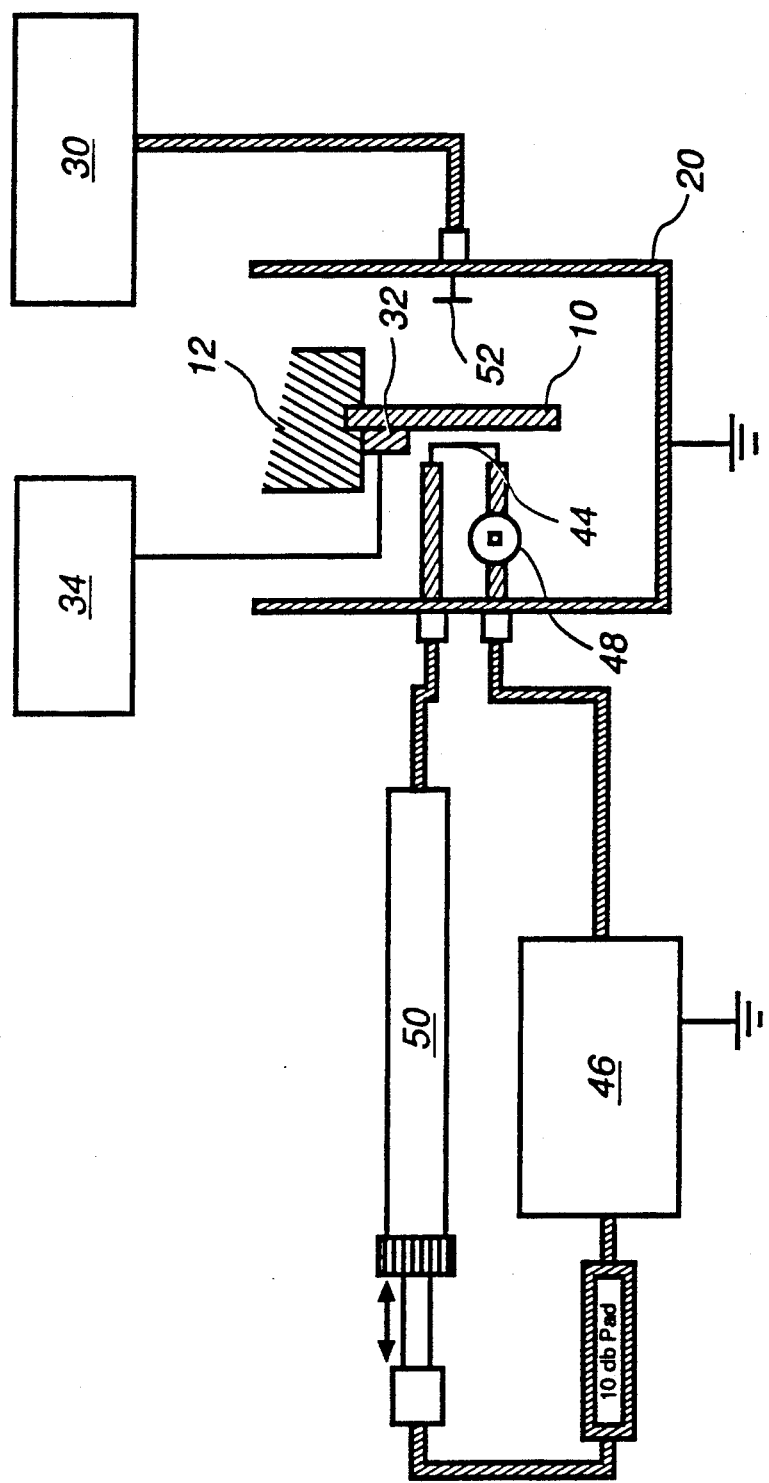
FIG. 6 is a schematic representation of the high frequency, single loop antenna embodiment of the present invention. Shown is the series-resonance circuit.
Figure 7:
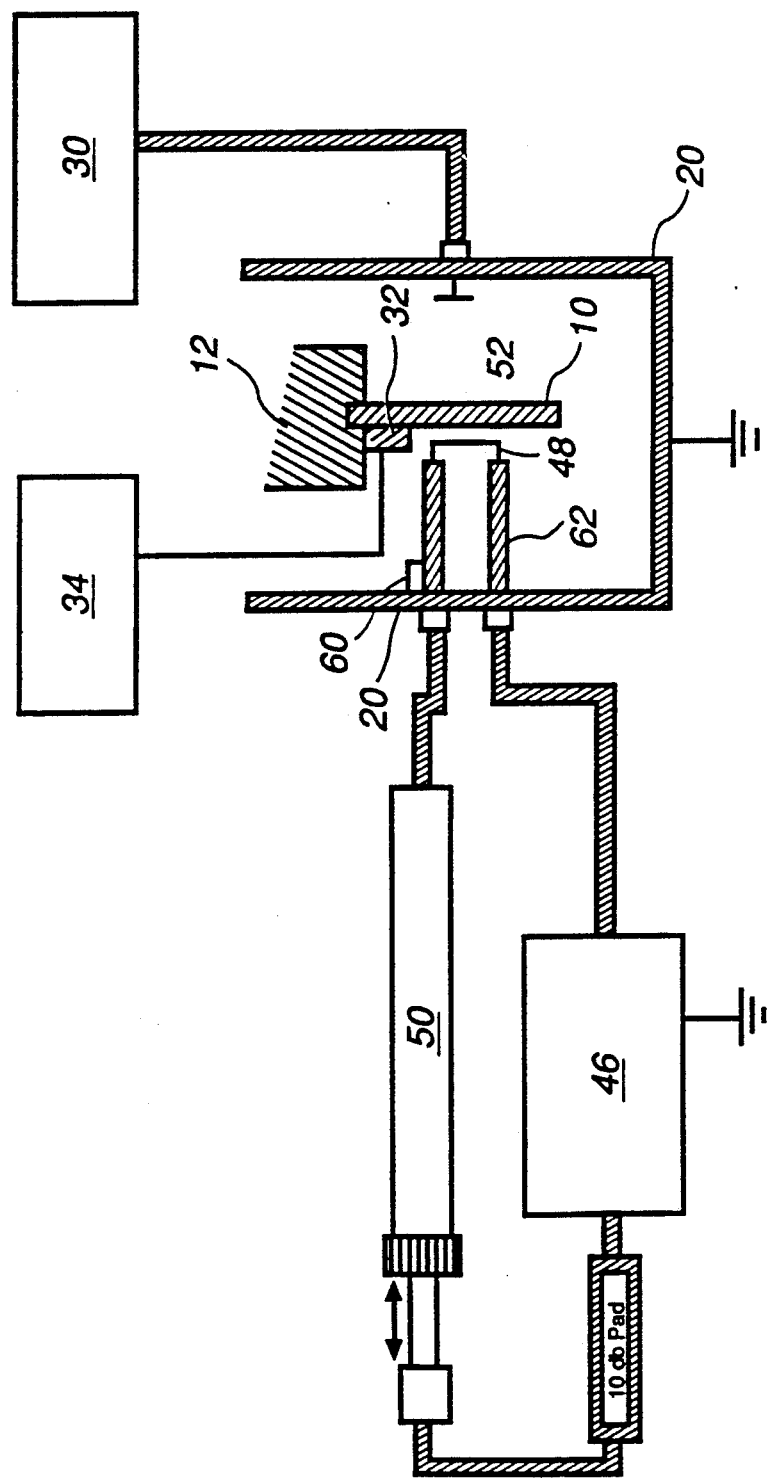
FIG. 7 is a schematic representation of a second high frequency single loop antenna embodiment of the present invention. Shown is the parallel-resonance circuit.

FIG. 6 and 7 show high-frequency embodiment of the present invention which employ a single sensor inductor 44 coupled to sample 10. Sensor self-inductance is reduced as a result of increased shielding currents as the sample becomes superconducting.

In FIG. 6, the single loop inductor 44 forms an oscillator when connected in series with line stretcher 50, wide-band rf amplifier 46 and series-tuning capacitor 48. Adjustment of capacitor 48 and line stretcher 50 determines the base value of resonant frequency. Capacitive probe 52 and counter 30 are used to determine the resonant frequency which varies with the self-inductance of sensor 44.

FIG. 7 shows a parallel-resonance embodiment of the present invention. Tap 60 on major inductive loop 62 provides feedback to amplifier 46, resulting in oscillation. A small section 48 of loop 62 has its self-inductance modified by variation in resistivity of sample 10. Tests with a single-turn inductor adjacent to copper and aluminum foils indicate that this approach can be used at frequencies in excess of 1.5 GHz. The single-coil, self-inductance method is particularly applicable to large-area films, films plated on thick substrates, films plated on lossy substrates, or on the inner walls of cavities.

The apparatus of the present invention has been found to produce characterizations of superconducting material resistivity that are currently unmatched in resolution when temperature is near or above the critical temperature. Resolution (for very high quality samples) is poorer for temperatures significantly below the critical temperature, since there is some residual leakage of magnetic field around the sample. This leakage makes it more difficult to resolve changes when increases in the shielding effect of the sample are small compared to the leakage field. Consider, for example, where 5% of the field bypasses a perfectly superconducting sample; it then becomes difficult to observe the difference in a further reduction, say, from 5.02% to 5.01% coupling as the sample changes from "mostly" to "completely" superconducting at temperatures well below the critical temperature. Clearly, the coil dimensions should be small compared to the sample dimensions to minimize the problem of leakage of fields around the sample.

Figure 8:
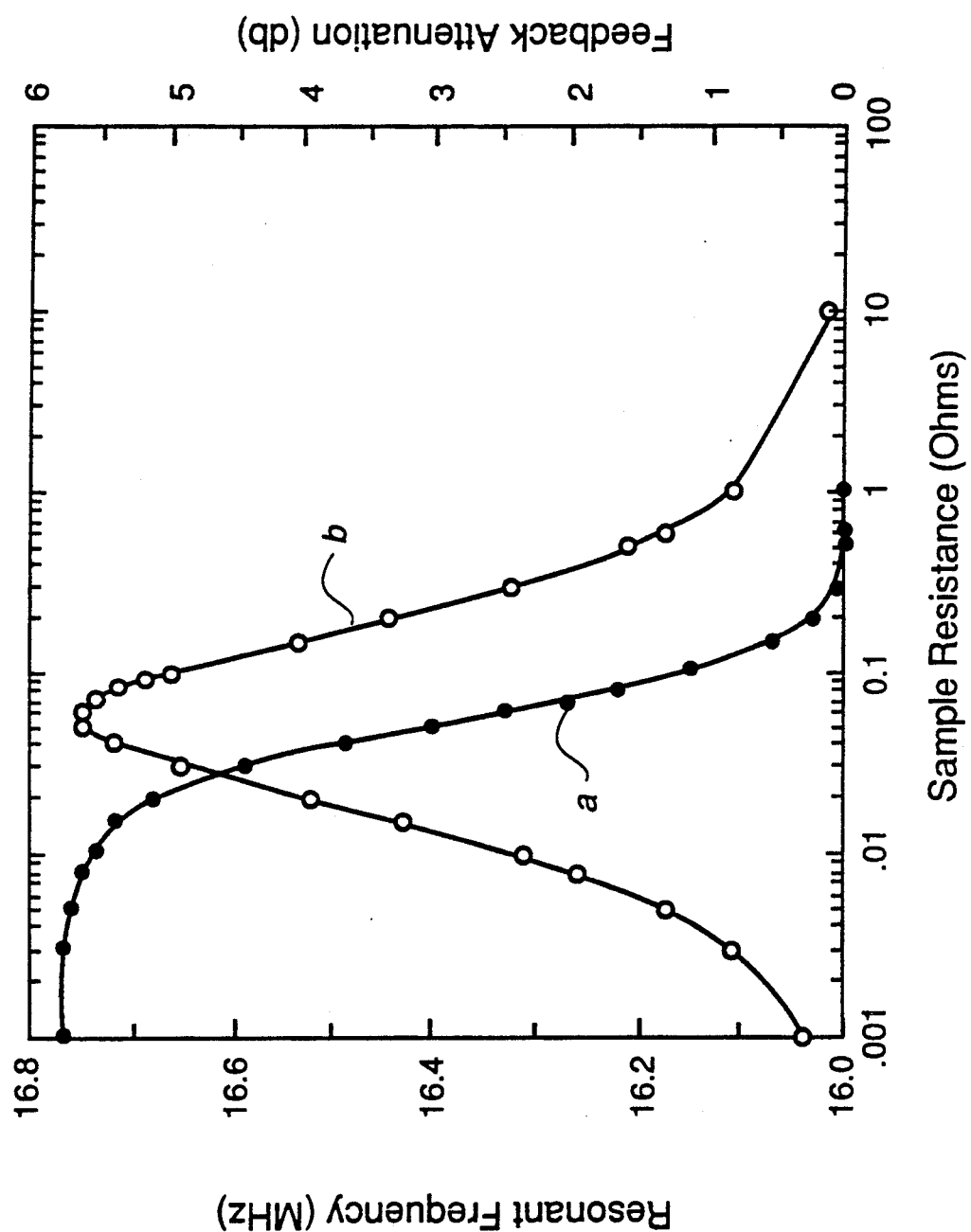
FIG. 8 shows traces of calculated oscillator frequency and feedback-loop attenuation, respectively, as a function of sample resistance.

Although the superconducting sample temperature versus frequency shift or induced voltage of FIGS. 3 and 5, respectively, demonstrate that the superconducting transition region of a sample may be characterized, it is with some difficulty that the actual resistivity of the sample may be related to these parameters (except for highly symmetric sample geometry). FIG. 8 shows calculations of oscillator resonant frequency and feedback loop attenuation as a function of toroidal sample resistance. These calculations apply to the circuitry of FIG. 1, hereof, where the coupling coefficient between each coil 14, 16 and sample 10 is 0.3, and where each coil is 20 turns of 32 gauge copper wire. A toroidal shape was chosen in order to simplify calculations. With more refined calculations, the measured results of FIGS. 3 and 5 may be, in principle, reduced to resistivity determinations for arbitrary by comparison of measurements of a sample (of unknown resistivity characteristics) with measurements on a sample (of known resistivity characteristics) which has the same geometry.

Figure 9A:
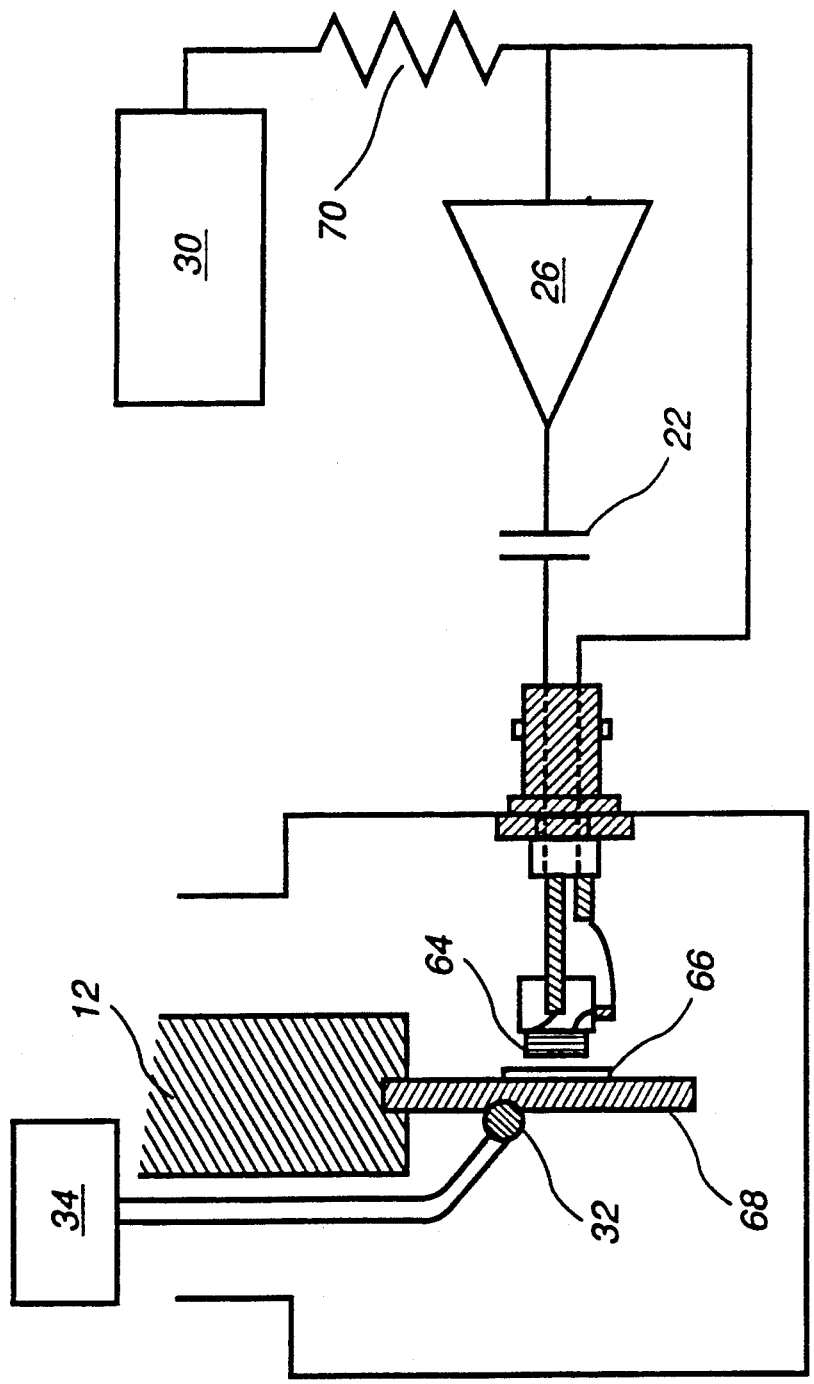
Figure 9B:
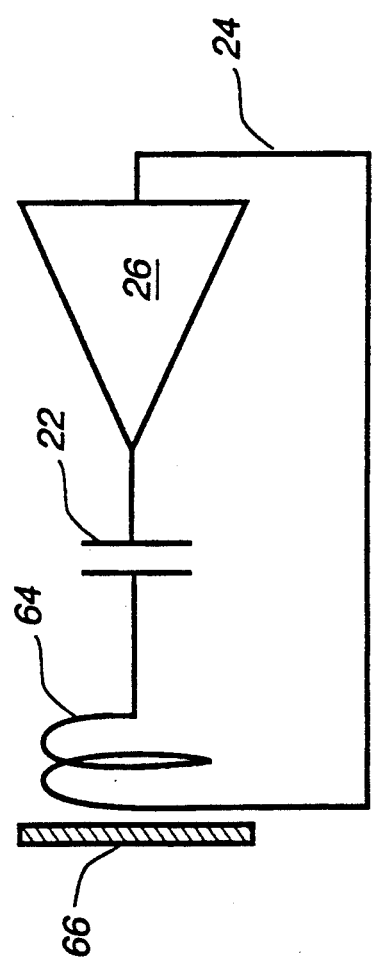
FIG. 9b illustrates the equivalent oscillator circuit therefor.

FIG. 9a shows a schematic representation of a single-coil embodiment of the present invention which is similar in concept and operation to the two-coil embodiment illustrated in FIG. 1 hereof. FIG. 9b describes the equivalent oscillator circuit for the apparatus of FIG. 9a. As stated hereinabove, a single sensing coil may be used to investigate surface conductivity of samples. In particular, self-inductance measurements are well-suited for studies of large-area films. Coil 64 having inductance $L_s$, is disposed in the vicinity of film 66 mounted on a substrate 68 of sapphire cooled by copper cold finger 12. The coil forms part of a feedback oscillator circuit 24 shown in FIG. 9b which includes capacitor 22 and amplifier 26. The frequency of oscillation is measured using counter 30 isolated from the oscillator by resistor 70. The coil, film, substrate, and copper cold finger are enclosed in vacuum chamber 20. Temperature of the sample substrate is measured by thermometer 32 which is read by reader 34.

The apparatus illustrated in FIG. 9 hereof does not require that the sample have any particular size or shape and, more particularly, does not require that the superconductor be "enclosed" by the sensor. The sensor may be much smaller than the sample and if made movable relative to the sample can be employed for high resolution mapping of a localized region of interest. Moreover, one surface of a sample may be measured independently of the other.

Advantages of the present invention over conventional four-lead resistivity measurements are as follows:

(1) No electrical contact with the sample is required. This is important for high-temperature superconducting materials, since electrical contacts are difficult to make and tend to modify the characteristics of the sample surface prior to measurement. This is a particularly serious problem for thin films, where the "surface" that is affected by direct contacts can be the entire sample thickness. The consequent lack of a need for contact preparation also significantly reduces the set-up time for measurements.

(2) Inherent in the frequency-shift measurements are low noise and high resolution. That is, measurement of an oscillator frequency to six or seven significant figures is to be compared with the two to four significant figures typical of measurements of very small ac or dc voltages in the direct-contact measurements. The low voltages observed in conventional direct-contact ac resistivity measurements on superconductors generally require that a complex, expensive phase-locked amplifier be employed.

(3) While conventional resistivity measurements will indicate zero resistance with only a single-filamentary superconducting path (which can represent an extremely small volume of the sample), the present invention measures "bulk" characteristics, at least to the skin or London penetration depth at the chosen frequency of operation.

(4) The frequency-shift measurement apparatus has minimal sensitivity to microphonics when the sample is positioned in the proximity of the center location between the coils.

The foregoing description of four preferred embodiments of the invention has been presented for purposes of illustration and description. It is not intended to be exhaustive or to limit the invention to the precise form disclosed, and obviously many modifications and variations are possible in light of the above teaching. For example, it would be apparent to one possessing ordinary skill in the art after having carefully reviewed the present disclosure that an apparatus capable of simultaneously measuring a plurality of samples might be useful for product analyses in the superconductivity industry. Moreover, said individual having skill in the art would recognize that a shunt-to-ground parallel resonant inductance-capacitance circuit could be used in place of the series-resonant circuit in the oscillators described hereinabove. The embodiments were chosen and described in order to best explain the principles of the invention and its practical application to thereby enable others skilled in the art to best utilize the invention in various embodiments and with various modifications as are suited to the particular use contemplate. It is intended that the scope of the invention be defined by the claims appended hereto.

What I claim is:

1. An apparatus for characterization of electrical conductivity of films, said apparatus comprising in combination support means for holding the film under investigation, electronic oscillator means having a series-resonant LC circuit, the inductive member thereof comprising inductive means disposed generally in the vicinity of the material under investigation and having the effective inductance thereof modified by magnetic fields generated by shielding currents induced in the film under investigation by the action of said inductive means, and counting means for measuring the frequency of oscillation of said electronic oscillator means.

2. The apparatus as described in claim 1, said electronic oscillator means thereof further comprising at least one capacitive element in series connection with said inductive means, and at least one amplifier means in series connection with said inductive means and said at least one capacitive element.

3. The apparatus as described in claim 1, wherein said inductive means includes a wire coil.

4. The apparatus as described in claim 3, wherein the physical dimensions of said inductive means is small compared with the physical dimensions of the material under investigation.

5. The apparatus as described in claim 1, further comprising cooling means for bringing said support means and the films under investigation to a chosen temperature, and temperature measuring means for determining the temperature of the film under investigation.

6. The apparatus as described in claim 5, further comprising vacuum chamber means for enclosing and for providing a reduced pressure environment to said inductive means, said support means, said cooling means, said temperature measuring means, and the film under investigation.

* * * * *